(12) United States Patent
Goff et al.

(10) Patent No.: US 11,446,728 B2
(45) Date of Patent: Sep. 20, 2022

(54) RADIAL COMPRESSION MECHANISM

(71) Applicant: Blockwise Engineering LLC, Tempe, AZ (US)

(72) Inventors: Edward Goff, Phoenix, AZ (US); Jeremiah J. Warriner, Tempe, AZ (US)

(73) Assignee: BLOCKWISE ENGINEERING LLC, Tempe, AZ (US)

( * ) Notice: Subject to any disclaimer, the term of this patent is extended or adjusted under 35 U.S.C. 154(b) by 0 days.

(21) Appl. No.: 17/391,646

(22) Filed: Aug. 2, 2021

(65) Prior Publication Data

US 2022/0016687 A1    Jan. 20, 2022

Related U.S. Application Data

(63) Continuation of application No. 16/491,188, filed as application No. PCT/US2019/015015 on Jan. 24, 2019, now Pat. No. 11,077,480.

(51) Int. Cl.
| | | |
|---|---|---|
| *B23P 19/04* | (2006.01) | |
| *B21D 39/04* | (2006.01) | |
| *A61F 2/95* | (2013.01) | |
| *B23P 11/00* | (2006.01) | |

(52) U.S. Cl.
CPC .......... *B21D 39/048* (2013.01); *A61F 2/9524* (2020.05); *B23P 11/005* (2013.01); *B23P 19/04* (2013.01)

(58) Field of Classification Search
CPC ..... B21D 39/048; B21D 39/04; B23P 11/005; B23P 19/04; B23P 11/00; A61F 2/9524; A61F 2/95; B21J 7/16; H01R 43/0424; H01R 43/0425; H01R 43/042; H01R 43/048; B25B 7/12
See application file for complete search history.

(56) References Cited

U.S. PATENT DOCUMENTS

| | | |
|---|---|---|
| 7,152,452 B2 | 12/2006 | Kokish |
| 7,618,252 B1 | 11/2009 | Goff |
| 8,056,218 B2 | 11/2011 | Nickol et al. |
| 8,245,559 B1 | 8/2012 | Warriner et al. |
| 9,757,232 B2 | 9/2017 | Peterson et al. |
| 9,821,363 B2 | 11/2017 | Goff |
| 2003/0056360 A1 * | 3/2003 | Brown .................... A61F 2/958 29/516 |

(Continued)

*Primary Examiner* — Sarang Afzali
*Assistant Examiner* — Darrell C Ford
(74) *Attorney, Agent, or Firm* — Invention To Patent Services; Alex Hobson

(57) ABSTRACT

A radial compression mechanism utilizes a string wrapped around a plurality of compression dies to move the dies inward and close a central cylindrical cavity defined by the working surfaces of the dies. The string may be coupled to a string tension mechanism that enables a user to applied a desired tension to the string and thereby compress an article within the central cylindrical cavity. The compression dies may be coupled to a base and move along die-guiding slots from an open position to a closed position. A spring may be configured to force the compression dies open and provide some back-tension to the string. The string may extend around a pully on an opposing side of the compression mechanism and both ends of the string may be coupled to the string tension mechanism.

20 Claims, 5 Drawing Sheets

(56) References Cited

U.S. PATENT DOCUMENTS

2016/0111841 A1* 4/2016 Battenfeld ................ B21J 7/16
    72/409.14
2022/0039979 A1* 2/2022 Castelli ................ A61F 2/9524

* cited by examiner

RADIAL COMPRESSION MECHANISM

CROSS REFERENCE TO RELATED APPLICATIONS

This application is a continuation of U.S. patent application Ser. No. 16/491,188 filed on Sep. 5, 2019 and currently pending, which is a national stage application of PCT application No. PCT/US2019/015015, having an international filing date of Jan. 24, 2019 and now expired, the entirety of both applications are hereby incorporated by reference herein.

BACKGROUND OF THE INVENTION

Field of the Invention

The invention relates to radial compression mechanisms and more specifically to mechanisms for compressing devices such as stents, catheters, balloons, and the like.

Background

In the manufacture and testing of medical devices, mechanisms are used to radially compress cylindrical devices such as stents, balloons, and catheters. For example, installation of a stent onto a catheter balloon is typically done by compressing the stent radially inward onto the balloon with enough pressure to permanently deform the stent to a smaller diameter and to slightly embed the metal stent into the plastic balloon. In another example, a polymer catheter balloon is compressed radially after pleating to wrap it tightly around the catheter shaft. In another example, a self-expanding stent is radially compressed to insert it into a sheath or delivery system. In another example, a stented, or metal-framed, prosthetic heart valve is compressed radially to deform and reduce the valve's metal structure and assemble it together with a delivery balloon catheter.

For some types of devices, such as prosthetic heart valves that include parts made from animal tissue, the crimping process is usually performed in the hospital's operating room, just prior to use of the medical device.

Large-diameter stents and balloons, such as aortic stents or prosthetic heart valves tend to require a large amount of radial force during the crimping process. The radial force applied to the product is equal to the surface area of the crimped product multiplied by the surface pressure. For example, a typical coronary stent is crimped to a size of about 1 mm diameter and 20 mm length while a typical prosthetic aortic heart valve is crimped to a size of about 6 mm diameter and 20 mm length. The heart valve has about six times more surface area than the coronary stent. Therefore, to reach the same surface pressure, about six times the radial force would be required.

For radial compression mechanisms that are actuated by human hand, or by a linear actuator such as an air cylinder, we can describe a "mechanical advantage" as the ratio of radial force applied to the processed product divided by the actuation force applied by the hand or actuator.

A first type of prior art device includes a radial compression mechanism wherein several similar wedge-shaped dies with planar surfaces are arranged to form an approximately cylindrical central cavity, the wedges being hinged and driven in unison to change the diameter of the cavity. An example of this mechanism is Machine Solutions Incorporated's hand-operated HV500 crimper, which, because of its low-cost injection-molded construction, should be suitable as a one-use, disposable, stent or prosthetic heart valve crimper for use in a sterile operating room. However, there are significant disadvantages to this crimper. The hinging, or pivoting dies have small pins that support the dies and transmit the forces, so the concentrated mechanical stress reduces the radial force capability of the device. The radial force is also limited because the handle moves through only a small distance of about 45 mm as the opening reduces from about 30 mm to about 6 mm, resulting in a very low mechanical advantage, and therefore inadequate radial force and pressure applied to the stent or heart valve.

A second type of prior art device includes a radial compression mechanism wherein several similar radially-movable dies with inward-facing surfaces are arranged to form an approximately cylindrical central cavity, the dies being constrained to move along radial lines, and being driven in unison by a rotating camming plate with pin/slot engagement to the dies, to change the diameter of the cavity. An example of this type of mechanism is described in U.S. Pat. No. 7,530,253B2 and is sold by Edwards Lifesciences Corporation as an injection molded, disposable prosthetic heart valve crimper for use in a sterile operating room. The use of a camming plate that rotates though a large, approximately 200 degrees, angle results in a mechanical advantage that is improved over the Machine Solutions crimper. However, further improvement in the mechanical advantage would be advantageous and would allow heart valves to be crimped to higher radial force, or pressure, resulting in a smaller size that is easier and less invasive for valve implantation procedures. Another shortcoming of this these crimping devices is that the radial force must be transmitted through the relatively small contact area between the slots of the camming plate and pins of the dies, which also limits the device's radial force capability.

There are many other examples of radial compression mechanisms, or crimpers, in which the radial forces must be transmitted through small pins and/or ball bearings that roll on cam surfaces, and in which the radial force that may be applied to the processed device is limited by the force that can be safely transmitted through the cam-following pins, bushings, or ball bearings.

It would be highly advantageous, therefore, to remedy the foregoing and other deficiencies inherent in the prior art.

SUMMARY OF THE INVENTION

An exemplary radial compression mechanism utilizes a string wrapped around a plurality of compression dies to move the dies inward and close a central cylindrical cavity defined by the working surfaces of the dies. The string may be coupled to a string tension mechanism that enables a user to applied a desired tension to the string and thereby compress an article within the central cylindrical cavity. The compression dies may be coupled to a base and move along die-guiding slots from an open position to a closed position. A spring may be configured to force the compression dies open and provide some back-tension to the string. A plurality of springs may be configured between the plurality of compression dies and they may be retained in position by spring seats configured on the compression dies, such as a post or recess.

An exemplary radial compression mechanism comprises a plurality of dies arranged in circular array around a central cavity. An exemplary radial compression mechanism may have a number of compression dies including, but not limited to, three or more, five or more, seven or more, ten or more, fifteen or more and any range between and including the number of dies provided. Each of the plurality of dies comprises an inwardly facing working surface and these working surfaces define the central cylindrical cavity. The working surfaces move with respect to each other and may touch and slide across each other or have a very small gap therebetween, such as no more than 1 mm, no more than 500 um, no more than 250 um, no more than 100 um, no more than 50 um, no more than 25 um and any range between and including the gap dimensions provided. The circular array of compression dies forms an outer perimeter along the outer surfaces of the dies. The string contacts the outer surfaces to move the dies inward.

An exemplary base of a radial compression mechanism comprises a die-guiding feature or slot to control the motion of compression dies. A die-guiding slot may be an aperture in a base member, a recess in a base member or a pair of rails or protrusions forming a slot therebetween. An exemplary base member may be configured on opposing sides of the compression dies and have corresponding die-guiding slots in each. It should also be noted that the system for guiding the die motion may be achieved with a wide range of design elements, including, but not limited to: 1) tabs or pins on dies engaging slots in stationary plates, as shown above, or 2) tabs or pins on the stationary plates engaging slots on the dies, or 3) cam-follower type ball bearings or plain bearings, engaging cam surfaces, or 4) ball bearings or plain bearings upon which the dies are mounted directly, so that the hinging point for the dies' motion is the bearing itself.

An exemplary string is a supple elongated member that such as a cord, rope, string, band and the like. In some embodiments however, a string may have a rectangular or irregular cross-sectional shape. An exemplary string may be made out of low friction materials, such a polymer such as plastic including but not limited to polyethylene, ultra-high molecular weight polyethylene, such as Spectra fiber available from Honeywell International Inc., nylon, fluoropolymer including fluorinated ethylene propylene (FEP), polytetrafluoroethylene, metal string or strands, stainless steel, and the like. An exemplary string may comprise a plurality of strands that are twisted, wrapped, or braided around each other or braided. An exemplary string may be a core-sheath type string having a core of one type of material and a sheath of another type of material. Note that low friction coatings or lubricants may be used with the string or applied to the string and/or the outer surface of the compression dies.

An exemplary string may be wrapped around the outer perimeter of the circular array of compression dies one or more times, such as two or more times, three or more times, four or more times, six or more time and any range between and including the number of wraps provided. An exemplary compression die may have a string guide configured along the outer surface to prevent the string from moving off the die and to keep the string aligned. A string guide may be a recessed area or a pair of protrusions spaced apart to allow the string to slide therebetween. The number of revolutions or wraps of the string around the compression dies increases the mechanical advantage, or the radial force imparted to the product for a given string tension. However, the total string-to-die friction also increases with the number of revolutions, so there are diminishing returns as more revolutions are added. Significant gains in mechanical advantage continue up to about four or five revolutions or wraps. It should also be noted that the actuating string may be designed in various arrangements, such as: removing the pulley, and anchoring one end the string to the fixed base, while pulling only the other end; or using two or more segments of string, pulling on one or both ends of each segment. It should also be noted that the string may contact the dies in various ways, such as within slots along the outside surface or along the outer surface, or through holes in the dies, so long as pulling the string and thereby reducing the perimeter of the string loops causes the central cavity to reduce diameter.

An exemplary radial compression mechanism may comprise a string tension mechanism that a user interfaces with to apply tension to the string and close the central cylindrical cavity. An exemplary string tension mechanism that has a handle for the user to manipulate to tension the string. An exemplary string tension mechanism may be a lever coupled to a pivot and pivoting the lever may apply tension to the string to close the cavity. An exemplary string tension mechanism may be a winch mechanism having a winch shaft that the string is attached to. The winch may have a winch crank that the user can turn or rotate to rotate the winch shaft and apply tension to the string. The string may wrap around the winch shaft as the central cavity is closed.

An exemplary radial compression mechanism comprises a pulley and the string may extend around the pulley to the guide the string from the string tension mechanism to the outer perimeter of the compression dies. A pulley may be configured on an opposing side of the radial compression mechanism and the string may extend from the string tension mechanism, around the pulley and then around the compression dies and then back to the string tension mechanism, whereby both ends of the string are attached to the string tension mechanism, such as the winch shaft. This arrangement may produce more uniform force to the compression dies as the string is being pulled or tensioned by both ends. It should also be noted that, although a hand-operated crank is shown here, there will likely be applications where the winch shaft may be more advantageously actuated by, for example, an electric motor or an air motor, with or without a gearbox.

A central cavity may have an open diameter that is large enough to receive an object for compression and the open central cavity diameter may be about 25 mm or more, about 50 mm or more, about 100 mm or more, about 150 mm or more and any range between and including the open central cavity diameters provided. A central cavity may be closed to be in a completely closed configuration, or may be limited to a certain diameter such as about 5 mm, or a diameter just sufficient to adequately compress the inserted article.

In an exemplary embodiment, the compression dies are forced open by a spring or springs. A spring or springs may be configured around the compression dies, such as around the outer diameter and may pull the compression dies open. As described herein, compression springs may be configured between the plurality of dies and the dies may have spring seats to retain the springs. It should also be noted that a variety of methods may be used move the dies outward, opening the central cavity, when the string is relaxed. These may include: 1) coil-type compression springs between the dies, as shown herein, or 2) leaf-type compression springs between the dies, or 3) springs between each die and a stationary frame member, which may be compression, tension, or torsion types. A spring may be a coiled spring as shown or an elastic material such as an elastomer or rubber material that can be elongated or compressed from an original shape by a load and will then return to said original shape upon removal of the load.

An exemplary radial compression mechanism including the dies, the base and the string tension mechanism may be made out of plastic and they may be injection molded plastic pieces to enable the radial compression mechanism to be a disposable part, such as the heart valve radial compression mechanism used in the operating before implantation of many heart valves.

Accordingly, it is an object of the present invention to provide a new and improved radial compression mechanism.

Another object of the invention is to provide a new and improved radial compression mechanism for compressing devices, such as large stents and prosthetic heart valves, that require high radial forces.

Another object of the invention is to provide a new and improved radial compression mechanism that can apply high radial forces and may be built with low-cost construction methods.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figure 1:
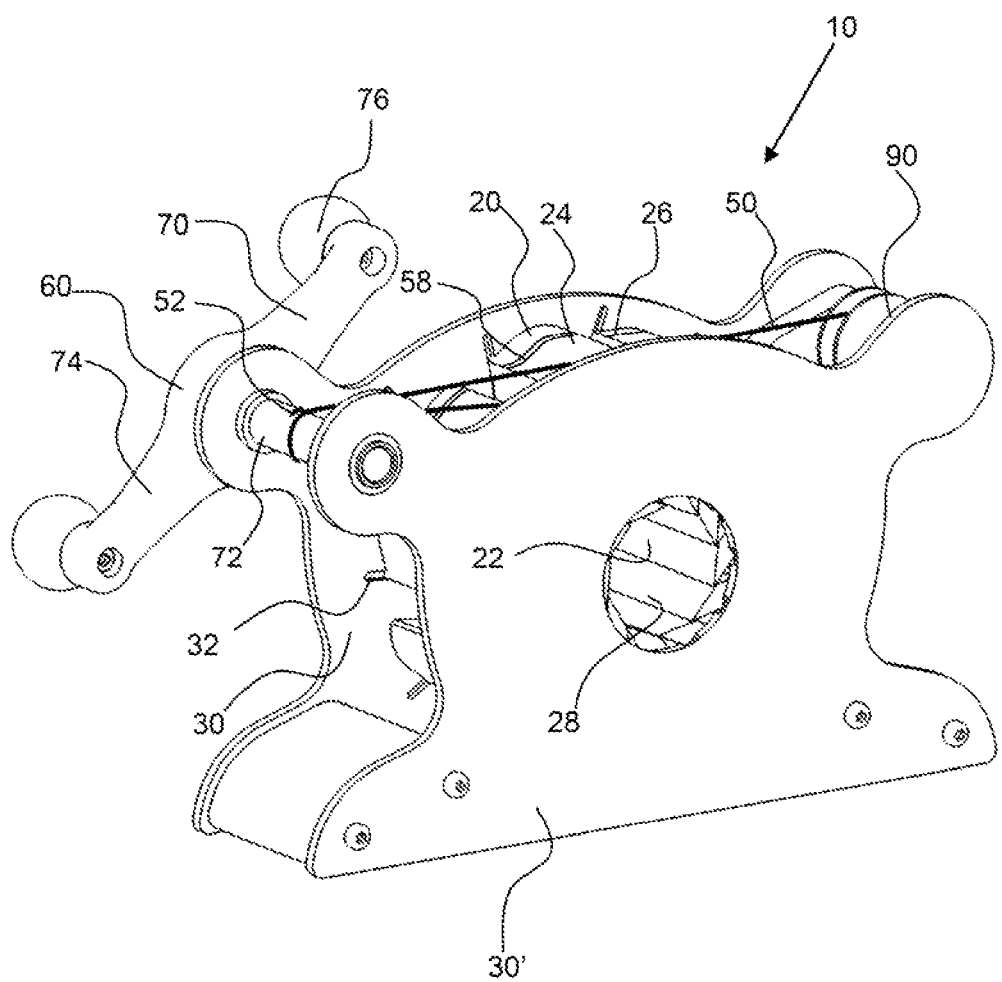
FIG. 1 shows a perspective view of the receiving side of an exemplary radial compression mechanism in a partly-open configuration.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Figure 2:
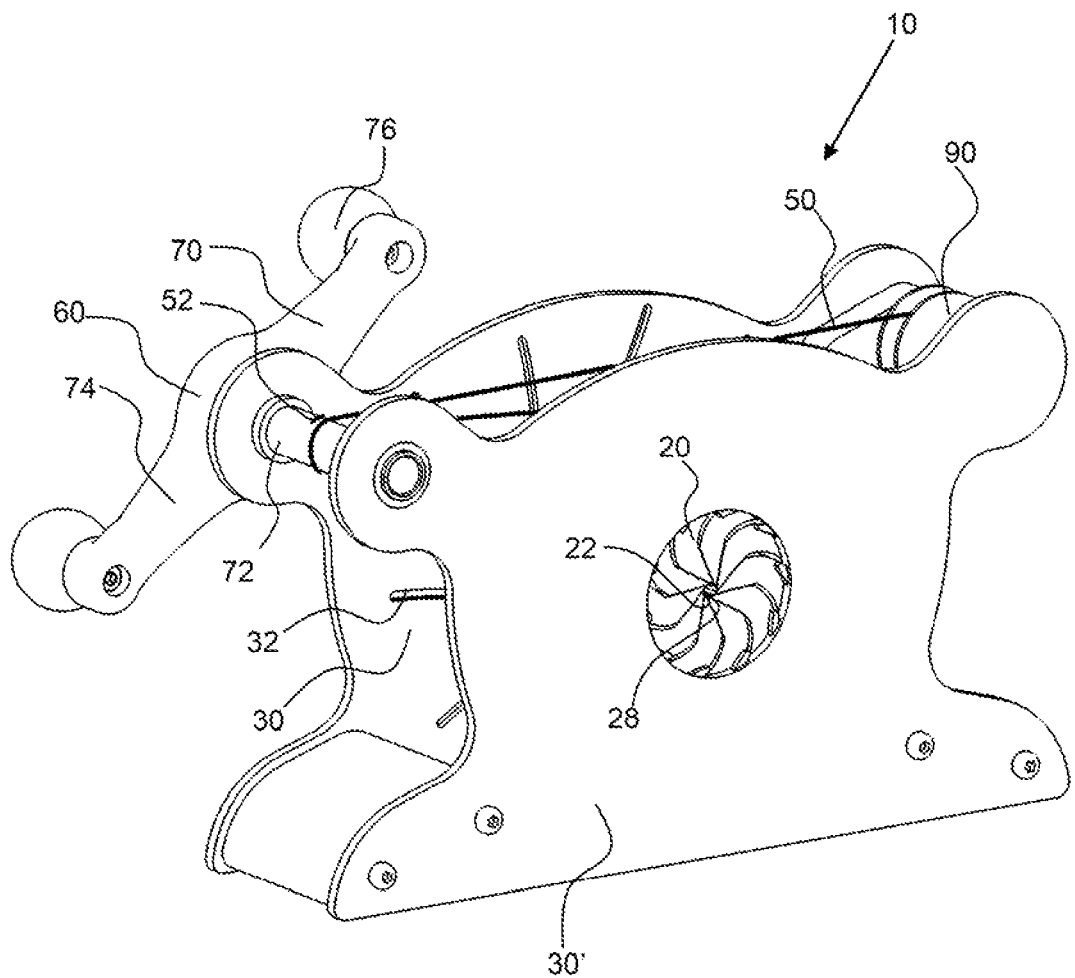
FIG. 2 shows a perspective view of the receiving side of an exemplary radial compression mechanism in a closed configuration.
Figure 3:
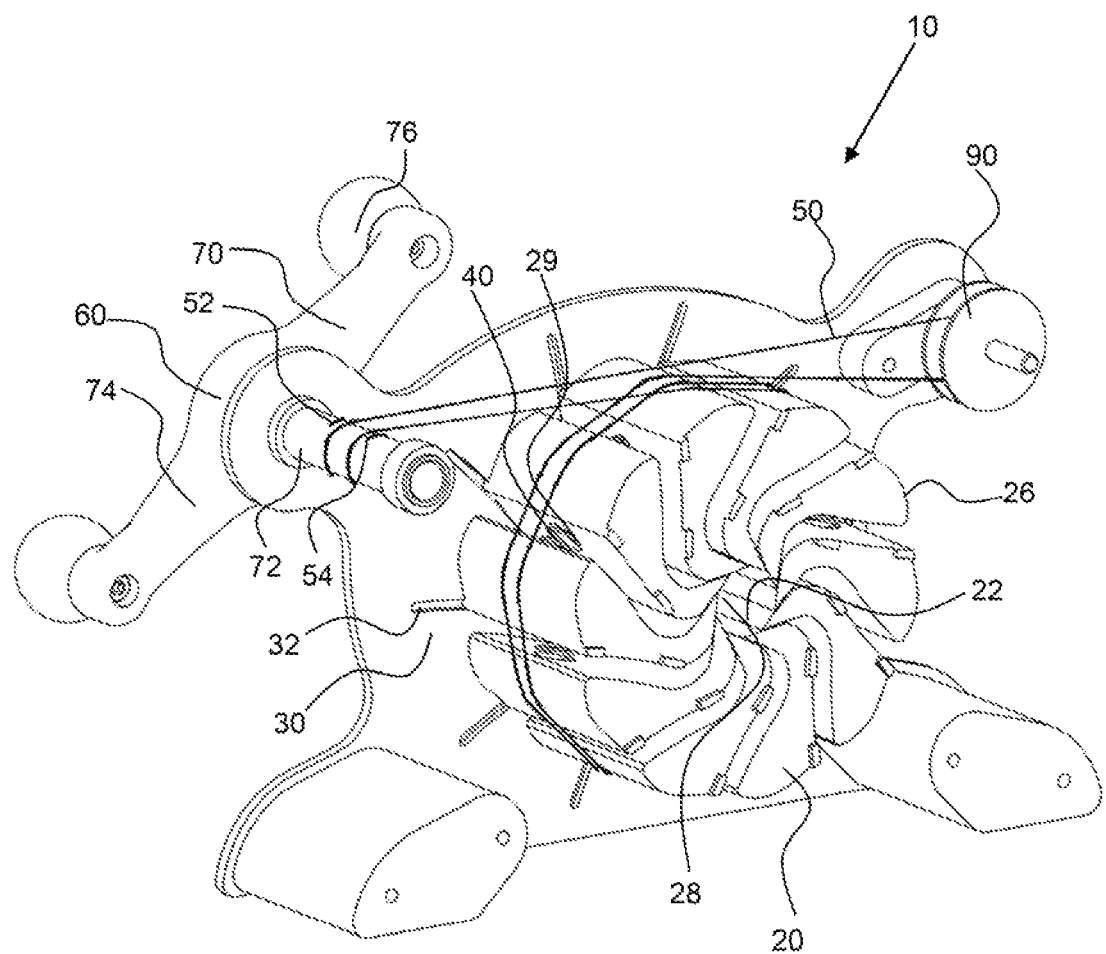
FIG. 3 shows a perspective view of the receiving side of an exemplary radial compression mechanism in a partly-open configuration and with a base member removed to reveal the string wrapped around the outer perimeter of the compression dies.

Referring to FIGS. 1 to 3, an exemplary radial compression mechanism 10 comprise a plurality of compression dies 20 coupled to a base 30 and arranged in a circular array around central cylindrical cavity 28 for receiving an object for compression. The base comprises a first base member 30 and second base member 30' on opposing sides of the compression dies; each of the base members comprising die-guiding slots 34 that constrain the dies to move approximately radially inward. Base member 30' has a receiving aperture for receiving an object into the central cylindrical cavity for compression. Ten compression dies are arranged in a circular array forming a cylindrically-shaped central product-receiving cavity. Each die has an inward-facing working surface 22 that cooperates with the other dies to form the central cylindrical cavity, and an outer surface 24 that forms the outer perimeter 26 of the arranged plurality of compression dies. FIG. 1 shows the radial compression mechanism in an open position with the compression dies open to form an open cavity diameter. FIG. 2 shows the radial compression mechanism in a closed position with compression dies in a closed to form a closed cavity diameter. A string 50 is wrapped around the outer perimeter 26 of the compression dies and is coupled with a string tension mechanism 60. The exemplary string tension mechanism is a winch mechanism 70 having a winch shaft 72 that rotates to apply tension to the string. The first end 52 of the string is attached to the winch shaft. A user may rotate the winch crank by the winch handle 76 to apply tension to the string and close the central cylindrical cavity 28. A string is wrapped around the array of dies, contacting each die on its outer face 24. In an exemplary embodiment the string 50 makes two or more complete revolutions around the array of dies. When the string is pulled, the string tension results in an inward force applied approximately equally to all the dies, causing the dies to move inward along the paths defined by the die-guiding slots 32 to decrease the diameter of the central cavity 28. The radial force applied to a product in the central cavity is roughly proportional to the tension in the string. The string contacts the dies over a relatively broad surface area, thereby providing a means to impart high radially inward forces to the dies, those forces in turn being transmitted from the dies to the product in the central cavity, By comparison with prior-art mechanisms that transmit forces through pins or bearing balls, the present invention can impart higher radial forces without damage to the mechanism. As shown in FIG. 1, a string guide 58 is configured along the outer surfaces of the dies to prevent the string from slipping off of the dies.

As shown in FIG. 3, the radial compression mechanism 10 has one of the base members removed revealing the actuation string encircling the outer perimeter 26 of the compression dies 20. The string 50 extends around the compression dies, around a pulley and back to the string tension mechanism 60. The string extends from the winch shaft 72, around the pulley 90 and is then wrapped around the compression dies before returning to the winch shaft. Both the first end 52 and the second end of the string 54 are attached to the winch shaft. The string is pulled by winding two ends of the string onto the rotatable winch shaft actuated to the winch crank 74. The pulley changes the direction of one of the two string ends, so that the two ends of the string approach the array of dies from opposite directions. This arrangement may provide a more uniform force on the plurality of compression dies.

As shown in FIG. 3, the working surfaces 22 intersect with each other, or nest with the adjacent die's working surface to produce the central cylindrical cavity 28. As the dies move in unison within the guiding slots 32, the diameter of the central cavity is changed. The guiding slots are shaped so that the dies move along a path that maintains a very small die-to-die gap at the periphery of the central cavity. The working surface and the slots may be designed to make the die-to-die gap any size and any function of central cavity diameter. depending on the requirements of the application, but for most applications it should be as small as possible while preventing direct rubbing contact of the die tips, in accordance with the achievable manufacturing tolerances of the parts. In some applications, direct rubbing contact of the adjacent die tips may be allowable or desirable.

As shown in FIG. 3, compression springs 40 are placed between the dies, pushing the dies outward against the string, and causing the central cavity to open as the string is relaxed. The springs produce a slight tension in the string to prevent it leaving the correct position. The dies may have spring seats 29, a recess or protrusion from the die to retain the spring in position. As the string is pulled and the central cavity is closed, there is friction between the string and each of the dies as the string slides across the outer surface 24 of the dies. Such friction limits the force that is transmitted to the product and should be minimized. In the preferred embodiment, the string is made of braided, fibrous, ultrahigh molecular weight polyethylene, which has a very low coefficient of friction against most materials.

Figure 4:
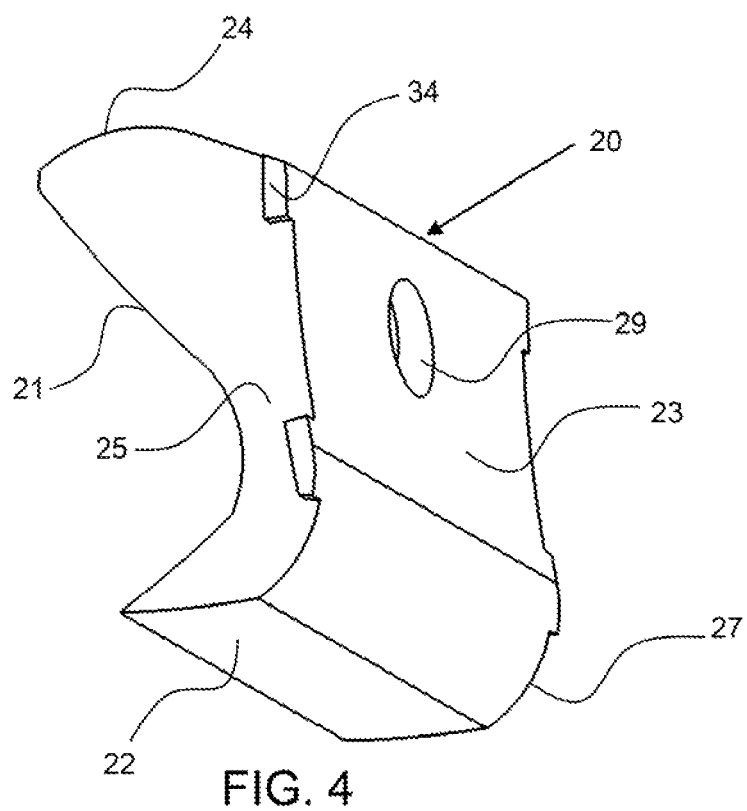
FIGS. 4 and 5 show perspective views of an exemplary compression die having a working surface, outer surface and a spring seat.
Figure 5:
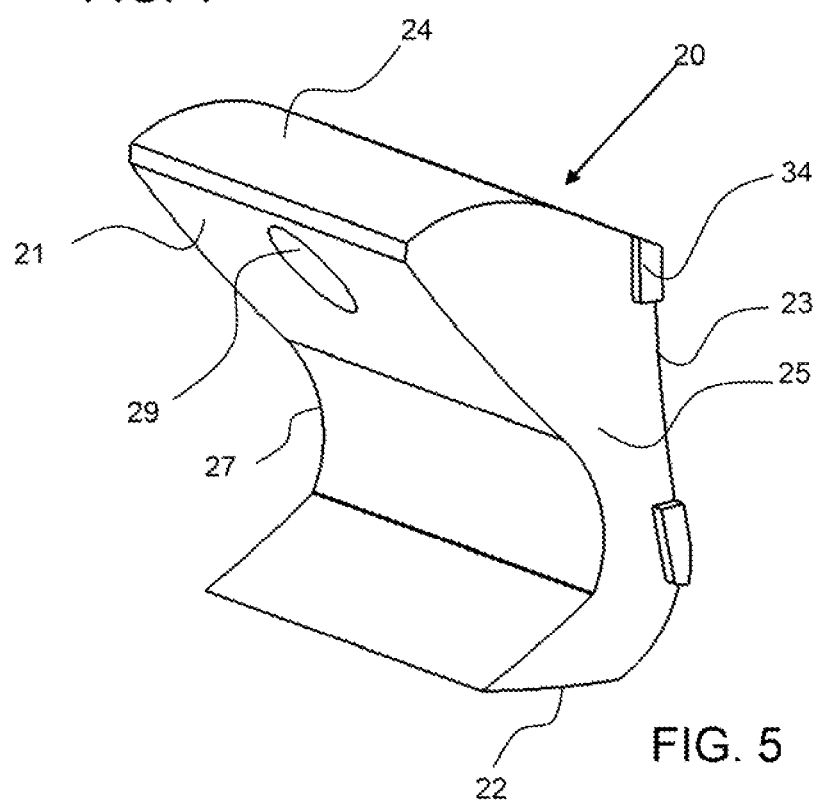

Referring now to FIGS. 4 and 5, an exemplary compression die 20 has a length from a working surface 22 to an outer surface 24, The compression die has a spring seat 29, a recess to retain the spring in position. The exemplary compression die has a width from a first face 21 to an opposing second face 23. The faces of the die are curved and have a geometry to allow nesting of the dies to produce the die array for movement about the central cylindrical cavity. The exemplary compression die has a depth from a first side 25 to a second side 27, which defines the depth of the central cylindrical cavity. Also, the exemplary die has a pair of guide post 34 extending from each side. The guide posts are configured for coupling with the die-guiding slots, such as by being inserted into the die-guiding slots.

Figure 6:
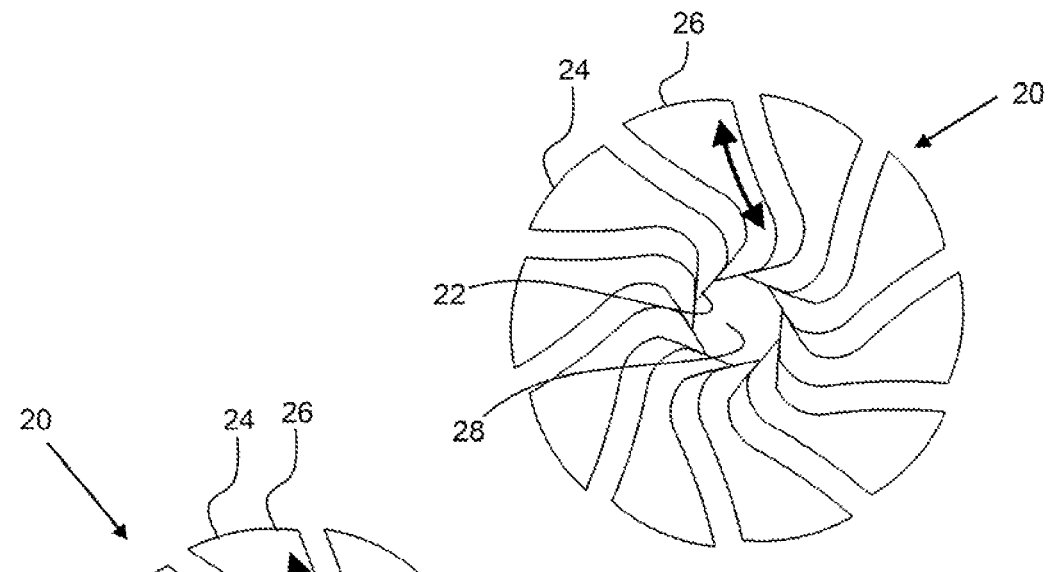
FIGS. 6 to 8 show compression dies configured for movement along various types of paths to close the central cylindrical cavity.

In the preferred embodiment, the guiding slots have curvature direction opposite to that of a spiral shape, constraining the dies to move in rotation about a virtual hinging point may lie outside the envelope of the die, but lies within the wedge-like shape formed by the working surface and the "back" surface. This results in a "backward" curving motion of the dies, as shown in FIG. 6. In this embodiment, the working surfaces must have a slightly convex shape to maintain near zero die-to-die gap throughout the opening and closing motion. This embodiment is also an embodiment of the mechanism described in U.S. Pat. No. 8,220,307.

Figure 7:
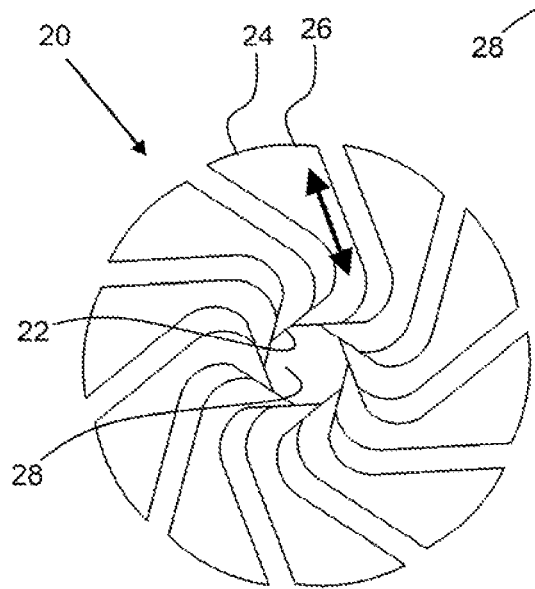

In another embodiment, the guiding slots are linear, constraining the dies to move in a linear path, as shown in FIG. 7. In this embodiment, the working surfaces must be flat to maintain near-zero die-to-die gap throughout the opening and closing motion.

Figure 8:
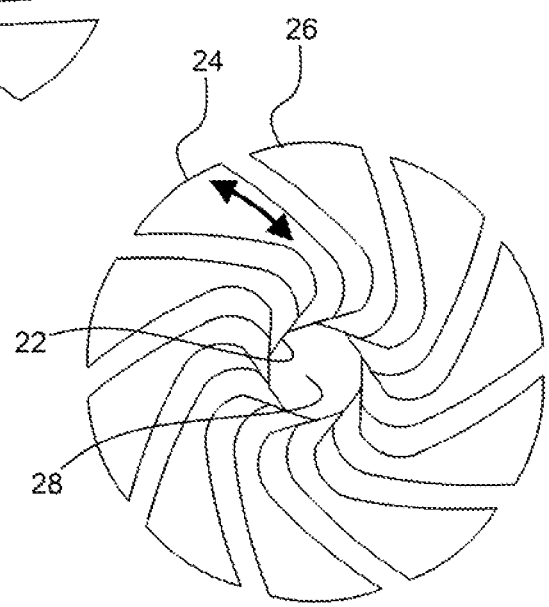

In another embodiment, the guiding slots have curvature in the same direction as a spiral shape, constraining the dies to move in rotation about a virtual hinging point may lie outside the envelope of the die, but lies opposite to the wedge-like shape formed by the working surface and the "back" surface. This results in a "forward" curving motion of the dies, as shown in FIG. 8. In this embodiment, the working surfaces must have a slightly concave shape to maintain near zero die-to-die gap throughout the opening and closing motion. This embodiment is also an embodiment of the mechanism described in U.S. Pat. No. 7,963,142.

It should also be noted that a winch shaft or drum is only one possible method for pulling one or more ends of the string. Other designs are possible, including, but not limited to: 1) manually pulling the strings with a human hand, or 2) using any kind of commonly available linear actuator, such as an air cylinder or electric motor with lead screw, or 3) gripping and pulling the string with pinch rollers or capstans.

Thus, a new and novel radial compression mechanism has been disclosed. The new and novel radial compression mechanism is constructed with a string or cable wrapped around the array of dies, the tension in the string causing radially-inward force on the dies and the product in the cavity. Therefore, the limited force capacity of prior art devices has been overcome.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A radial compression mechanism comprising:
a) a base;
b) a plurality of compression dies arranged in a circular array about a central axis, each comprising:
  i) an inward facing working surface; and
  ii) an outer surface;
  wherein said plurality of compression dies form a central cavity having a cylindrical shape defined by the working surfaces;
c) a string wrapped one or more revolutions about the circular array of the plurality of compression dies that contacts each of the plurality of compression dies;
  wherein the plurality of compression dies are coupled to said base and configured to move in unison from an open position, wherein the central cavity has an open cavity diameter, radially inward to a closed position wherein the central cavity has a closed cavity diameter;
  wherein pulling of the string forces the plurality of compression dies to move in unison from said open position to said closed position; and
  wherein said open cavity diameter is larger than said closed cavity diameter;
  wherein the radial compression mechanism is configured to produce a radially inward compression force along the working surfaces of the plurality of compression dies from an open position to a closed position; and wherein the central cavity maintains the cylindrical shape from said open position to said closed position.

2. The radial compression mechanism of claim 1, wherein the string is wrapped four or more times around the circular array of the plurality of compression dies.

3. The radial compression mechanism of claim 1, further comprising a string tension mechanism, wherein the string is coupled to the string tension mechanism and wherein actuating the string tension mechanism pulls the string to move the plurality of compression dies radially inward to close the central cavity.

4. The radial compression mechanism of claim 3, wherein the string has a first end and a second end and wherein both the first and second ends of the string are coupled to the string tension mechanism.

5. The radial compression mechanism of claim 4, further comprising a pulley and wherein the string extends from the string tension mechanism around the pulley and then around the plurality of compression dies.

6. The radial compression mechanism of claim 3, wherein the string tension mechanism is a winch mechanism comprising:
a) a winch shaft;
b) a winch crank;
wherein the string is coupled to the winch and wherein actuating the winch pulls the string to move the plurality of compression radially inward to close the central cavity.

7. The radial compression mechanism of claim 6, wherein the string has a first end and a second end and wherein both the first or second ends of the string are coupled to the winch mechanism.

8. The radial compression mechanism of claim 7, further comprising a pulley and wherein the string extends from the string tension mechanism around the pulley and then around the plurality of compression dies.

9. The radial compression mechanism of claim 3, wherein the string tension mechanism is a lever mechanism comprising:
a) a lever pivot;
b) a lever arm that rotates about the lever pivot;
wherein the string is coupled to the lever and wherein actuating the lever pulls the string to move the plurality of compression dies radially inward to close the central cavity.

10. The radial compression mechanism of claim 9, wherein the string has a first end and a second end and wherein both the first end and second end of the string are coupled to the lever mechanism.

11. The radial compression mechanism of claim 10, further comprising a pulley and wherein the string extends from the string tension mechanism around the pulley and then around the plurality of compression dies.

12. The radial compression mechanism of claim 1, wherein the string has a first end and a second end and wherein the string is wrapped around the circular array of the plurality of compression dies with at least one of the first or second ends coupled to the base.

13. The radial compression mechanism of claim 1, further comprising a spring coupled to the plurality of compression dies to force the central cavity open.

14. The radial compression mechanism of claim 1, further comprising a spring configured between each of the plurality of compression dies to force the plurality of compression dies apart and the central cavity open.

15. The radial compression mechanism of claim 14, wherein each of the plurality of compression dies comprise a seat to receive and retain an end of said spring.

16. The radial compression mechanism of claim 1, comprising at least three compression dies.

17. The radial compression mechanism of claim 1, wherein each of the plurality of dies has an outer surface and wherein the string extends around said outer surface of each of the plurality of dies.

18. The radial compression mechanism of claim 1, wherein the plurality of dies are backward curving dies.

19. The radial compression mechanism of claim 1, wherein the plurality of dies are linear dies.

20. The radial compression mechanism of claim 1, wherein the plurality of dies are forward curving dies.

* * * * *